(12) United States Patent
Martin

(10) Patent No.: US 7,674,440 B2
(45) Date of Patent: Mar. 9, 2010

(54) APPARATUS FOR BIO-DECONTAMINATION OF ENCLOSURES

(75) Inventor: Anthony Martin, Andover (GB)

(73) Assignee: Bioquell UK Limited, Andover, Hampshire (GB)

( * ) Notice: Subject to any disclaimer, the term of this patent is extended or adjusted under 35 U.S.C. 154(b) by 0 days.

(21) Appl. No.: 10/583,882

(22) PCT Filed: Dec. 17, 2004

(86) PCT No.: PCT/GB2004/005313

§ 371 (c)(1),
(2), (4) Date: Jun. 21, 2006

(87) PCT Pub. No.: WO2005/061010

PCT Pub. Date: Jul. 7, 2005

(65) Prior Publication Data

US 2007/0053813 A1    Mar. 8, 2007

(30) Foreign Application Priority Data

Dec. 22, 2003   (GB)   ................... 0329725.6

(51) Int. Cl.
*A61L 2/00* (2006.01)
*B01L 1/04* (2006.01)
*B08B 15/00* (2006.01)

(52) U.S. Cl. .................. 422/295; 454/187; 454/49

(58) Field of Classification Search .................. 422/295; 454/187, 49–67
See application file for complete search history.

(56) References Cited

U.S. PATENT DOCUMENTS

| 3,503,703 A | | 3/1970 | McDonald et al. |
|---|---|---|---|
| 4,249,463 A | * | 2/1981 | Hornby ....................... 454/57 |
| 4,601,885 A | * | 7/1986 | McClure ..................... 422/114 |
| 5,160,700 A | | 11/1992 | Anderson et al. |
| 5,229,071 A | | 7/1993 | Meo, III |
| 5,711,705 A | * | 1/1998 | Krainiak et al. ............... 454/57 |
| 5,906,794 A | * | 5/1999 | Childers ....................... 422/28 |
| 6,368,206 B1 | * | 4/2002 | Hunter et al. .................. 454/58 |
| 2002/0168305 A1 | * | 11/2002 | Morrow et al. ............ 422/186.3 |
| 2003/0086820 A1 | | 5/2003 | McDonnel et al. |
| 2004/0184950 A1 | * | 9/2004 | McVey et al. ................... 422/4 |

FOREIGN PATENT DOCUMENTS

| WO | WO 0211774 A1 | * | 2/2002 |
|---|---|---|---|
| WO | WO 03/082355 A1 | | 10/2003 |
| WO | WO 03082355 A1 | * | 10/2003 |

* cited by examiner

*Primary Examiner*—Sean E Conley
*Assistant Examiner*—Kevin C Joyner
(74) *Attorney, Agent, or Firm*—Workman Nydegger

(57) ABSTRACT

An enclosure (23) for carrying out operations under sterile conditions having apparatus for sterilising the enclosure and its content includes a gas generator (17,18) having a fan (18) for producing a stream of air and an evaporator (17) for evaporating hydrogen peroxide solution to be carried by the airstream throughout the enclosure to condense on surfaces in the enclosure to sertilise the surfaces. A pump (13) is provided to draw gas from the enclosure at a location remote from the gas generator to ensure that the sterile vapour reaches the most remote part of the enclosure from the generator and also to maintain the pressure in the generator below atmospheric pressure around the generator so that any leak path in the enclosure results in leakage from the atmosphere into the enclosure and not release of sterilant vapour to atmosphere outside the enclosure.

18 Claims, 3 Drawing Sheets

APPARATUS FOR BIO-DECONTAMINATION OF ENCLOSURES

BACKGROUND OF THE INVENTION

1. Field of the Invention This invention relates to apparatus for the bio-decontamination of enclosures and in particular small enclosures.

2. Present State of the Art

U.S. Pat. No. 5,229,071 discloses a batch method and apparatus for controlled release of gaseous air contaminants into the atmosphere through catalytic oxidation while minimizing both the energy required and the volume of waste gas exhausted into the atmosphere. The device has a recirculating gas stream driven by a recirculation fan which moves gas, normally and naturally present at start-up, through a bed of granular catalyst, in an oxidizer and into contact with the surface of a process-gas heater and back to the recirculation fan. The gaseous contaminants may be drawn into this system using a vacuum pump.

U.S. Pat. No. 5,160,700 discloses a sterilizing system including a sealed container for holding a gaseous sterilant under pressure and a first enclosure made at least partially of a gas-permeable material. The container and the articles to be sterilized are disposed in and sealed within the first enclosure, and the container, while in the sealed first enclosure, is manipulated to release gaseous sterilant into the sealed first enclosure. A second enclosure in which the first enclosure is disposed is constructed such that the sterilant released into the first enclosure from the container diffuses through the gas-permeable material of the first enclosure into the second enclosure at a rate capable of establishing sterilizing conditions in the first enclosure during a sterilizing cycle to thereby effect sterilization of the articles in the first enclosure. A moisture-releasing humidifying device is disposed within the first enclosure for releasing moisture into the first enclosure during the sterilization cycle and a regulating system comprising an exhaust device is operable to exhaust the sterilant gas from the second enclosure to minimize the amount of sterilant gas in the second enclosure, thereby providing for minimized residue sterilant in the surrounding work area.

US-A-2003/0086820 discloses that a surface which carries a material which is infected with prions is cleaned with an alkaline cleaning solution to remove as much proteinaceous material as possible from, the surface. The solution contains an alkaline cleaning agent which attacks prions remaining on the surface and which also attacks prions removed from the surface during the cleaning step. After the cleaning step, the surface is exposed to a strong gaseous oxidant, preferably hydrogen peroxide vapor. The hydrogen peroxide or other strong oxidant attacks the prions, particularly the unclumped prion strands, deactivating the prions.

U.S. Pat. No. 3,503,703 discloses a sterilizing apparatus having a gas impermeable barrier and a flexible, collapsible gas impermeable bag having an aperture for receiving articles to be sterilized adapted to be mounted in gastight connection with the barrier. The bag is connected to the barrier in a gastight relationship and exhaust means are provided for reducing the internal pressure in the bag and for circulating air in the bag and valving and controls are provided for carrying out a sterilizing cycle in the bag.

Small enclosures are typically up to about 2 $m^3$ in volume, and include but are not limited to Class II Microbiological Safety Cabinets (MSC). Our International Patent Application PCT/GB03/001386 discloses methods of bio-decontaminating larger enclosures such as rooms or chambers by placing an apparatus to generate the fumigant gas inside the chamber. The technique described works well for rooms and large chambers of a simple nature but is not specifically intended to deal with the problems associated with Class II microbiological safety cabinets and similar enclosures.

The standard technique for bio-decontaminating a Class II MSC is to boil formalin to generate formaldehyde vapour. For this method to be effective substantial amounts of formalin have to be evaporated, the European Standard EN BS 12469 requires 60 ml of formalin plus 60 ml of water to be evaporated for each cubic meter of enclosure volume. Other authorities use smaller amounts of liquid but all of the methods used generate considerable amounts of condensation within the MSC and also form deposits of paraformaldehyde.

Formalin gassing of an MSC has a number of disadvantages; firstly it leaves a residue of formalin and paraformaldehyde that can only be removed by long periods of aeration; secondly the bio-decontamination process is slow, the normal exposure time being eight hours; thirdly it is difficult to ensure that the gas has reached all parts of the MSC especially in the filter plenum, fourthly the vapour is toxic with an Occupational Exposure Limit of 1 ppm, and lastly special precautions have to be taken to avoid leakage of the gas from the MSC, and in some installations the laboratories have to be evacuated during the fumigation process. An alternative to formalin fumigation that overcomes these problems would be of considerable value to laboratory personnel, and one choice of fumigant is hydrogen peroxide vapour providing that it can be deployed in a way which is safe for the user, since it is residue free, is effective and is fast acting.

It may be expected that some of the same difficulties that are encountered with formalin will also be encountered when using hydrogen peroxide as a fumigant. Most, if not all, MSCs leak to some extent. Introducing gas inside a chamber is accompanied by a rise in temperature which causes an increase in internal pressure. This rise in pressure, unless it is controlled, leads to leakage of the fumigant gas to the outside giving rise to a potential hazard to laboratory staff. Hydrogen peroxide and formaldehyde have similar diffusion constants and so it may be expected that the rate at which these two gases would diffuse around the enclosure would be similar. In an MSC it may be expected that bio-decontamination of the plenum chamber using hydrogen peroxide vapour may take some considerable time unless techniques are used to cause the gas to travel into the plenum.

The main advantages of using hydrogen peroxide as the fumigant gas are the facts that it does not leave a residue and that once an adequate gas concentration has been reached the process is very fast. Many, if not most, Class II MSCs that are in use recirculate their exhaust air back to the laboratory, and hence a method is required to remove the hydrogen peroxide vapour at the end of the bio-decontamination cycle.

SUMMARY OF THE INVENTION

The present invention is a technique to overcome these problems and provide a safe and reliable way to bio-decontaminate small enclosures including MSCs.

This invention provides an enclosure for carrying out an operation under sterile conditions having a first apparatus disposed within the enclosure for generating and delivering a sterilant vapour from a supply held within the enclosure to condense on surfaces throughout the enclosure to sterilise the surfaces, and means to draw gas from the enclosure at a location remote from the apparatus for delivering the sterilant to the enclosure to ensure that the sterilant vapour reaches the most remote part of the enclosure from the location where the sterilant is delivered to the enclosure and to maintain the enclosure at a predetermined pressure below atmospheric so that any leak paths result in leakage from the atmosphere into the enclosure and do not release sterilant vapour to atmosphere around the enclosure.

In accordance with one embodiment of the invention the means for drawing gas from the enclosure comprise a fan located in a conduit connected to an outlet from the enclosure, the conduit having means to render sterilant reaching the conduit ineffective to avoid release of sterilant to atmosphere.

Preferably the means to render the sterilant ineffective are located upstream of the fan in relation to the enclosure.

More specifically the means to render the sterilant ineffective may comprise a catalytic converter for breaking the sterilant down into harmless biproducts which can be exhausted to atmosphere.

It is also preferred that the conduit has selectively operable valve controlled outlets of larger and smaller capacities, the smaller capacity outlet being open during said period when the enclosure is to be maintained at a predetermined reduced pressure and the larger valve controlled outlet being opened during discharge of the sterilant atmosphere from the enclosure.

In any of the above arrangements, the enclosure may have a main chamber containing said apparatus for producing sterilant vapour and within which the operation to be carried out in the chamber is performed and a plenum chamber separated from the main chamber by a filter, the plenum chamber having a pump for delivering air into the plenum chamber through the filter to the main chamber to create a filter flow of air through the chamber and the means for drawing gas from the chamber remote from the first apparatus is connected to the plenum chamber.

In the latter arrangement a filter may be provided in the outlet from the plenum chamber to the means for drawing gas from the plenum chamber.

Also in any of the above arrangements the enclosure may contain a second apparatus for rendering sterilant in the atmosphere in the chamber ineffective after the sterilisation of the chamber.

In the latter construction the means for rendering sterilant ineffective may comprise a housing containing a catalytic converter for converting the sterilant into harmless biproducts for disposal and means for circulating the atmosphere of the chamber through the housing to reduce the sterilant concentration in the atmosphere when the sterilisation operation has been performed.

BRIEF DESCRIPTION OF THE DRAWINGS

The following is a description of some specific embodiments of the invention, reference being made to the accompanying drawings in which.

DETAILED DESCRIPTION OF THE PREFERRED EMBODIMENTS

Figure 1:
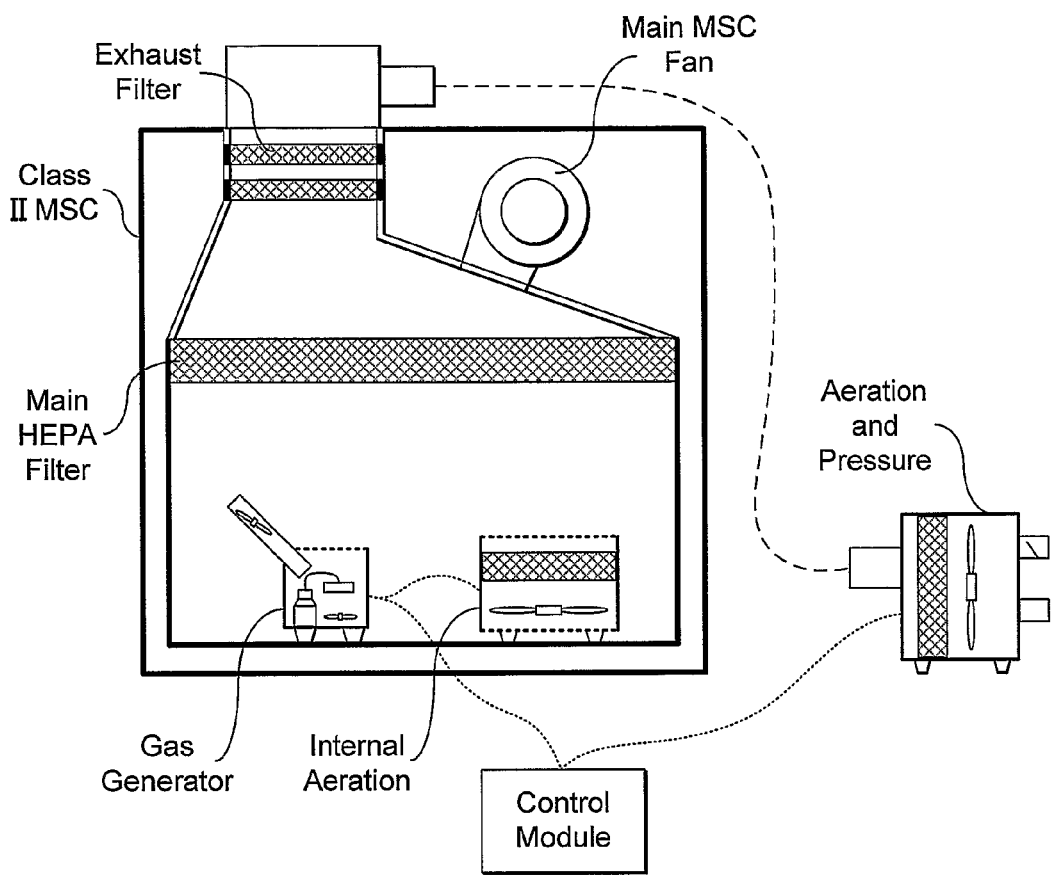
FIG. 1 is a schematic view of a Class II Microbiological Safety Cabinet incorporating an internal sterilant vapour producing device, an internal vapour decomposition device and an external pressure regulation and aeration system.

The apparatus is made up from three parts. The first part is a gas generator as disclosed in our International Patent Application GB03/001386. The gas generator is placed inside a main chamber of a cabinet. In the following description this will be an MSC, but it could be any small enclosure. Placing the generator inside the enclosure has the considerable advantage that holes do not have to be made in the MSC to connect supply and exhaust gas hoses. The generator consists of a hot plate, maintained at a temperature in excess of the boiling point of the aqueous hydrogen peroxide solution, onto which the solution of hydrogen peroxide is fed. A stream of air and gas mixture is blown across the heated plate to drive the vapours into the main chamber of the MSC. Also housed in the gas generator is the bottle containing the hydrogen peroxide solution, the volume of solution in the bottle is adjusted so that it is sufficient when evaporated to bio-decontaminate the MSC. This volume will vary according to the size and type of MSC. Attached to the gas generator is an external fan, set to drive the air/gas mixture from the main chamber through the internal pathways of the MSC. This ensures that the hydrogen peroxide and water vapour reach the internal plenum of the MSC.

The second unit is also placed inside the main chamber of the MSC and may be used to remove the hydrogen peroxide vapour at the end of the gassing cycle. This second unit works by passing the air gas mixture through a catalyst bed thus decomposing the hydrogen peroxide to water and oxygen.

The third unit is placed outside the MSC and has the dual function of maintaining a negative pressure during the gassing phase of the bio-decontamination cycle and afterwards may be used to remove the air/gas mixture rendering the exhaust gas harmless, by decomposing it to water and oxygen.

All three of these parts of the system are connected to a central control unit which is placed outside the MSC, giving the operator complete control of the process. A single electrical cable connects the units inside the MSC to the control system.

Experimental work has been carried out to see if it is possible to bio-decontaminate an MSC while maintaining it under negative pressure to minimise outward leaks and thereby ensuring a safe environment around the MSC. It is also desirable to reduce the time taken for bio-decontamination to a minimum using an automated cycle which can run without any input from the operator once the cycle had been started.

The specification for fumigation with formaldehyde requires that the main down flow fan inside the MSC has to be run during the gassing cycle. This means that either the MSC has an automated formaldehyde gassing cycle or the operator is required to attend during the cycle to switch the fan on and off. The reason for operating the fan is to ensure that the formaldehyde gas reaches the main plenum chamber. Ideally the cycle should not require an operator to attend until the cycle is completed.

In the experimental procedure a gassing cycle was arranged in four phases, the first to allow the equipment to stabilise, the second to evaporate the required amount of aqueous hydrogen peroxide solution thus raising the gas concentration and causing the formation of condensation on the surfaces, the third to maintain the chamber in this condition for a sufficient period of time to ensure bio-decontamination to the required standard, and finally the fourth to remove the air/gas mixture rendering the chamber safe.

A series of experiments were conducted to establish the best gassing cycle and equipment configuration to achieve a reliable bio-decontamination in the shortest possible time. The tests were conducted using a Class II MSC with the cabinet configured to recirculate the air back to the laboratory and also to duct the exhaust air to the outside. When in the recirculatory configuration it is essential that the exhaust air returned to the laboratory contains less than 1 ppm of hydrogen peroxide. If the exhaust air is to be exhausted to the outside it is possible to use the MSC extract fan to remove the hydrogen peroxide vapour, and thus reduce the aeration time.

There are two reasons for wanting to bio-decontaminate an MSC, they are to ensure that the working chamber is free of biological contamination and hence will not contaminate any experimental work undertaken inside the Cabinet, and the second is to ensure that the whole MSC is free of biological contamination so that the necessary maintenance operations, such as a filter change, may be undertaken without risk to the service and laboratory staff.

The tests reported here show the difference in the amount of liquid required to bio-decontaminate the chamber as compared with the whole MSC. This difference is a measure of the difficulty of achieving total bio-decontamination. For a test to be considered to give a satisfactory result it had to be conducted three times and give consistent results. The table below shows a summary of these tests.

| Configuration | Ducted | Recirculatory | Ducted | Recirculatory |
|---|---|---|---|---|
| Pressure Point | Chamber | Top | Top | Top |
| Liquid Volume ml | 10 | 15 | 65 | 65 |
| Bio-decontamination | Chamber | Chamber | All | All |
| Total Cycle Time min. | 36 | 85 | ? | 160 |

Pressure control of the MSC is critical not only to contain the active gas but may also be used to distribute the active gas throughout the whole MSC. In the first test reported above the pressure control point was in the wall of the main chamber of the MSC, but by moving this control point to the top of the MSC as in tests 3 and 4 the active gas is caused to circulate to all areas of the MSC. Negative pressure control is achieved by extracting a small amount of the active gas, thus causing the gas to move towards the pressure control point, and hence by placing the control point at the greatest distance from the injection point the gas is distributed throughout the whole MSC. A similar argument would apply to any complex chamber.

Further confirmation of the effects caused by the extraction point may be seen from the table below, which shows the gas concentration in the top fan plenum Chamber. The readings were taken at intervals of 5 minutes, and a note was taken of the highest value.

| Top Pressure Control Ppm | Chamber Pressure Control Ppm | Time Minutes |
|---|---|---|
| 0 | 0 | 0 |
| 34 | 7 | 10 |
| 79 | 12 | 20 |
| 85 | 7 | 30 |
| 120 | 9 | 40 |
| 159 | 13 | 50 |
| 183 | 18 | 55 |
| 763 | 124 | 60 |
| 902 | 448 | Maximum |

It can be seen from the above table that the gas concentration in the remote part of the MSC is much higher with the pressure control in the top of the cabinet than when it is in the chamber. This improved gas distribution leads to a reliable and faster bio-decontamination throughout the whole of the MSC. As stated above a similar technique would work for other types of complex chambers.

The apparatus of the invention is composed of four parts to minimise the weight of a single component so that it may easily be carried and set up by one person. These four parts will now be described in turn in conjunction with the method of operation with reference to FIGS. 2, 3, 4 and 5. The configuration shown in these diagrams is intended to be illustrative and not exclusive. There are a number of alternative configurations of enclosure which would allow changes to the set up.

Figure 5:
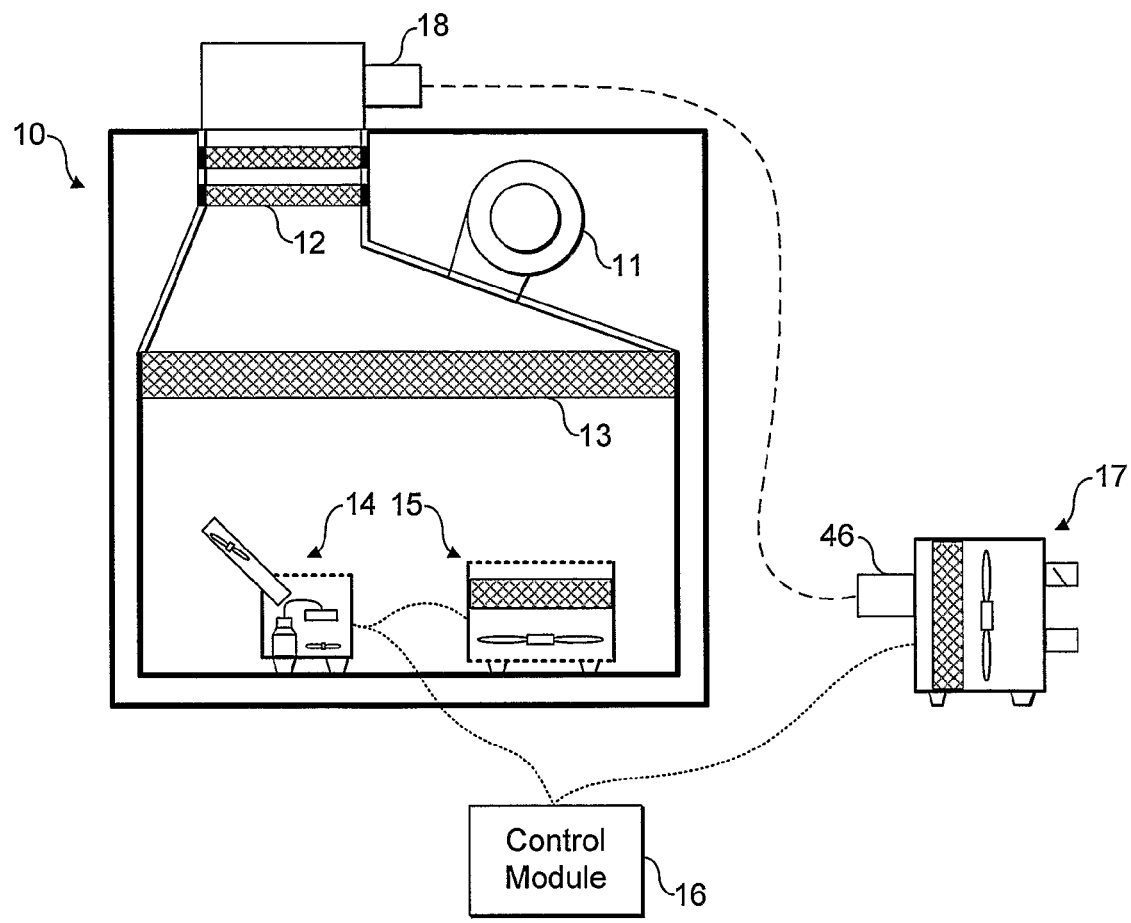
FIG. 5 is a schematic view of the complete apparatus of FIG. 1 in operational mode.

Before proceeding to a detailed description of the individual components of the apparatus an overview will be given with reference to FIG. 5 which depicts a typical Class II MSC 10 with an internal fan 11, a down flow filter 13 and an exhaust filter 12. Class II MSC are constructed in accordance with EN BS 12469, and generate a vertical down flow of air that has passed through a sterilising filter. In one construction a proportion of the air is exhausted to the outside. In another construction a proportion of the air is recirculated to the room through the filter 12. The cabinet is so constructed that the outer surface is under negative pressure thus preventing leakage of gas from the cabinet to the room. FIG. 5 depicts a typical set up for the latter construction, that is a recirculating cabinet.

A hydrogen peroxide generator 14 and a small aeration unit 15 are placed inside the main chamber of the MSC 10. They are connected to a control module 16 that is outside the MSC by an electrical cable. An external pressure control and aeration unit 17 are placed outside the MSC and also connected to the control unit 16. A further duct connection is made to the pressure control and aeration unit so that air may be exhausted from a spigot 18 at the top of the MSC.

The method of operation of each of these components will now be described with reference to FIGS. 2 to 4 of the drawings.

Figure 2:
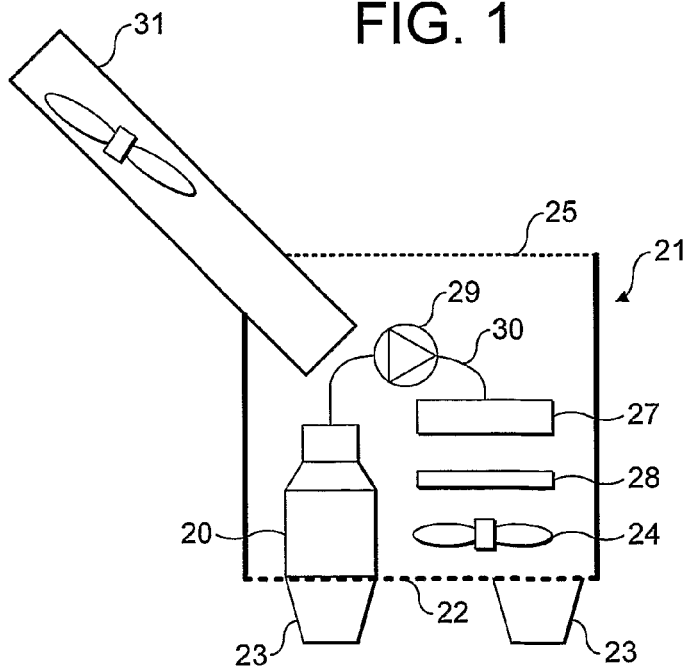
FIG. 2 is a more detailed schematic view of the sterilant vapour producing device of FIG. 1.

The evaporation unit is shown in FIG. 2, and consists of a liquid reservoir 20 housed in a case 21 with a perforated top 25 and bottom 22 to allow air to freely pass through the case. The case is mounted on feet 23 to minimise contact with the surface and allowing free passage of air all round the external surfaces. A fan 24 draws air in at the bottom of the case and causes a flow of air over the internal components and then to exhaust from the top of the case 25.

A heater 28 is placed in the air stream to raise the temperature of the air. A heater plate 27 is positioned above the air heater 28 on to which hydrogen peroxide solution is delivered by a pump 29 and pipe 30. The hydrogen peroxide solution is evaporated on the heated plate 27 which is maintained at a temperature above the boiling point of the solution. The heated air stream carries the water and hydrogen peroxide vapours out of the case 21, and part of this hot air/vapour stream is deflected by the external fan 31. In order to achieve rapid and reliable bio-decontamination it is essential that the vapours are distributed to all areas of the chamber while they are still hot. The purpose of the fan 31 is to ensure the distribution of the vapours immediately that they emerge from the generator. In Class II MSCs the air from the working chamber is drawn under the work surface and then up to the fan 11 (see FIG. 5). The fan 31 may be used to direct the hot vapours into this space. A more detailed explanation of the gas distribution system is provided at the end of the description of the apparatus.

Figure 3:
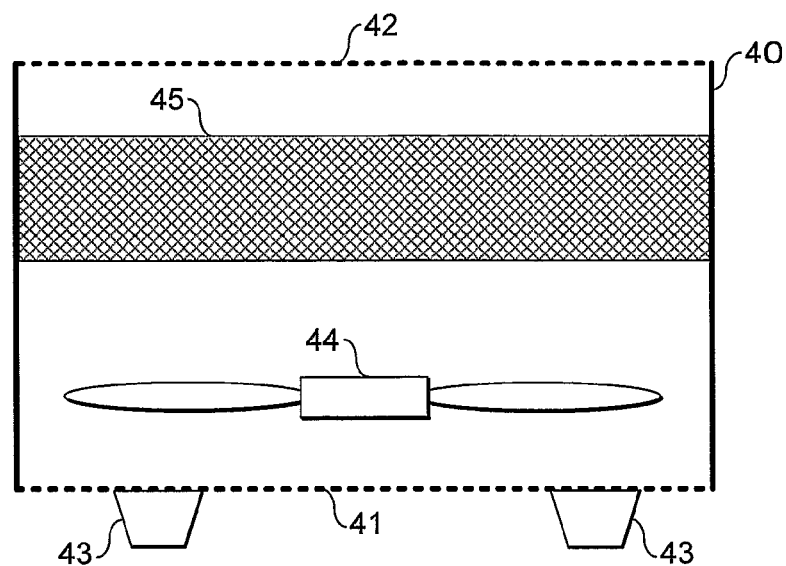
FIG. 3 is a more detailed schematic view of the vapour decomposition device of FIG. 1.

The internal aeration unit shown in FIG. 3 is used to decompose the hydrogen peroxide vapour to water and oxygen at the end of the bio-decontamination cycle. The unit is contained in a case 40 with a perforated base 41 and top 42 to allow the free passage of air through the unit. It is mounted on feet 43 again to permit the free passage of air all round the unit. Inside the case is a fan 44 which draws the air/gas mixture in at the bottom and forces it through the catalytic bed 45 that decomposes the hydrogen peroxide vapour, thus reducing the concentration of the vapour inside the Class II MSC by dilution.

Figure 4:
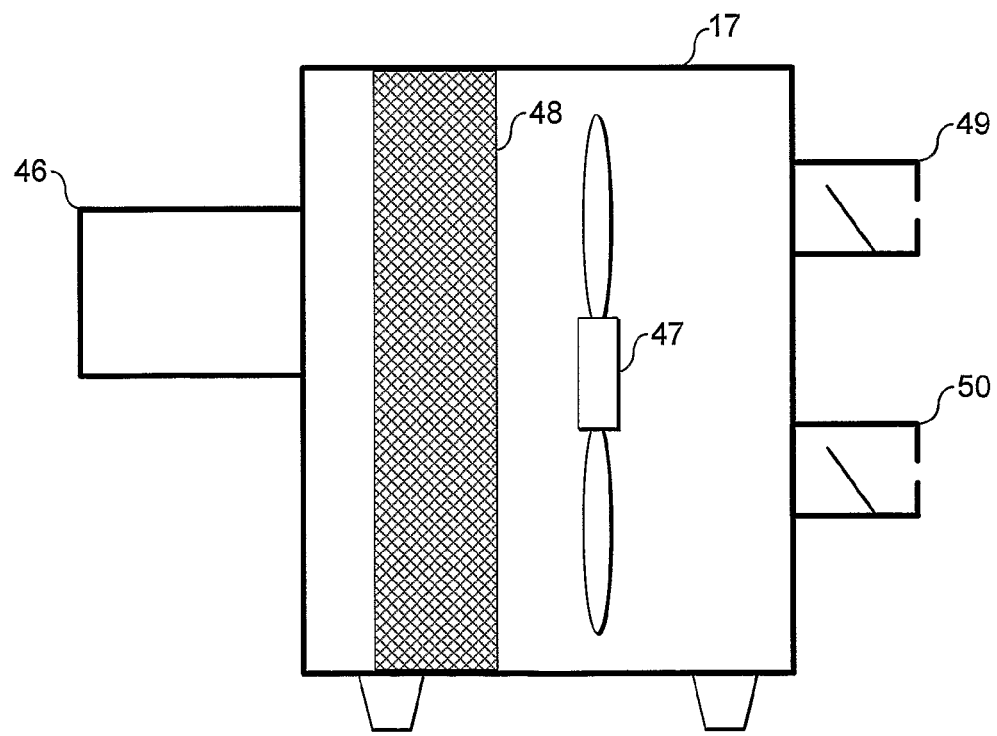
FIG. 4 is a more detailed schematic view of the external pressure regulation/aeration system of FIG. 1.

The external pressure control and aeration unit 17 is shown in FIG. 4. The duct 18 at the top of the Class II MSC 10 is connected to an inlet port 46 to the aeration unit 17, and a fan 47 draws air/vapour mixture from the Class II MSC throughout the whole of the bio-decontamination cycle. The air is drawn through a catalytic bed 48 to render the air stream free of harmful hydrogen peroxide vapour. During the gassing phase of the cycle a small amount of air leaves the pressure control aeration unit via a restriction valve 49. This valve is used to control the extract air and hence the internal pressure in the Class II MSC at the same time as causing the hydrogen peroxide vapour to be pulled to the most remote part of the chamber, thus ensuring bio-decontamination in this area. Once bio-decontamination has been achieved the valve 50 is opened and the air flow considerably increased. This increased air flow removes the air/hydrogen peroxide mixture from the inside of the Class II MSC thus reducing the aeration time. During the gassing phase of the cycle the extract air flow will generally be less than 10 $m^3$ per hour and during aeration this will rise to about 200 $m^3$ per hour. In order to increase the air flow during the aeration phase it is necessary to allow air into the Class II MSC, this may be achieved by opening the front window of the cabinet by a small amount. In other cabinets a special opening is provided that may be used to allow the inward airflow that is sealed during gassing.

There are a number of alternative configurations of the apparatus, firstly it is not necessary to have the internal aeration unit, although it is helpful in reducing the gas concentration at the start of aeration and avoids the need to open the cabinet to allow an extract system to be operated.

For cabinets that are connected to an exhaust duct the external aeration unit may not be required as the hydrogen peroxide vapour may be vented to the outside using the cabinet fans that have a greater capacity and hence provide a shorter aeration period. It is however still necessary to have a pressure control unit to ensure that the cabinet is maintained at negative pressure and that the gas is properly distributed.

Distribution of the active gas is critical to bio-deactivation process, and because the rate of diffusion is slow it is necessary to use mechanical means, such as fans or extraction, to ensure that the gas reaches all parts of the chamber. In EN BS 12469 for MSC it is suggested that during formaldehyde fumigation that the cabinet internal fan is operated for a short period to move the fumigant to the remote areas of the cabinet. This has the disadvantage of generating high pressure zones inside the cabinet with the consequent risk of leakage.

The fan 31 shown in FIG. 2 is attached to the evaporator combined with the pressure control extraction system overcomes this problem by direction the hot gas directly into the internal passageways of the chamber. The pressure control system then draws the active gas to the remote parts of the chamber.

The invention claimed is:

1. An enclosure for carrying out an operation under sterile conditions, the enclosure comprising:
    a main chamber;
    a first apparatus disposed within the main chamber for generating and delivering a sterilant vapour from a supply held within the main chamber to be distributed throughout the main chamber to sterilise the surfaces of the main chamber;
    a plenum chamber;
    a filter separating the plenum chamber from the main chamber;
    a pump for the plenum chamber for delivering air into the plenum chamber and then through the filter to the main chamber to create a filtered flow of air through the main chamber; and
    means for drawing gas from the enclosure via an outlet from the plenum chamber to create a flow of sterilant vapour from the main chamber through the filter to decontaminate the filter and through the plenum chamber to the outlet to sterilise the plenum chamber before exiting the outlet and to maintain pressure in the main and plenum chambers below atmospheric so that any leak paths result in leakage from the atmosphere into the chambers and do not result in release of sterilant vapour to the atmosphere around the enclosure;
    wherein the flow of air into the main chamber and the flow of sterilant vapour out of the main chamber pass through the same filter;
    wherein the means for drawing gas from the enclosure comprises a fan located in a conduit connected to the outlet; and
    wherein the conduit has means for rendering sterilant flowing through the conduit ineffective to avoid release of sterilant to atmosphere.

2. An enclosure as claimed in claim 1, wherein the means for rendering the sterilant ineffective is located upstream of the fan in relation to the enclosure.

3. An apparatus as claimed in claim 2, wherein the means for rendering the sterilant ineffective comprises a catalytic converter for breaking the sterilant down into harmless biproducts which can be exhausted to atmosphere.

4. An enclosure as claimed in claim 3, wherein the conduit has selectively operable valve controlled outlets of larger and smaller capacities, the smaller capacity outlet being open during said period when the enclosure is to be maintained at a predetermined reduced pressure and the larger valve controlled outlet being opened during discharge of the sterilant atmosphere from the enclosure.

5. An enclosure as claimed in claim 2, wherein the conduit has selectively operable valve controlled outlets of larger and smaller capacities, the smaller capacity outlet being open during said period when the enclosure is to be maintained at a predetermined reduced pressure and the larger valve controlled outlet being opened during discharge of the sterilant atmosphere from the enclosure.

6. An enclosure as claimed in claim 1, wherein a second filter is provided in the outlet from the plenum chamber.

7. An enclosure as claimed in claim 1, further comprising a second apparatus for rendering sterilant in the atmosphere in the main chamber ineffective after the sterilisation of the main chamber, the second apparatus being disposed within the main chamber.

8. An enclosure as claimed in claim 7, wherein the second apparatus comprises:
  a housing containing a catalytic converter for converting the sterilant into harmless biproducts for disposal; and
  means for circulating the atmosphere of the main chamber through the housing to reduce the sterilant concentration in the atmosphere when the sterilisation operation has been performed.

9. An enclosure as claimed in claim 1, wherein the outlet from the plenum chamber contains an exhaust filter through which air/sterilant vapour is drawn from the chamber.

10. An enclosure as claimed in claim 1, wherein the outlet from the plenum chamber contains two spaced filters through which sterilant vapour is drawn from the plenum chamber.

11. An enclosure as claimed in claim 1, wherein a second filter is provided in the conduit connected to the outlet from the plenum chamber.

12. An enclosure as claimed in claim 1, wherein the filter separating the plenum chamber from the main chamber is a HEPA filter.

13. An enclosure as claimed in claim 1, wherein the filter separating the plenum chamber from the main chamber is an air filter.

14. An enclosure as claimed in claim 1, wherein gas can travel in and out of the main chamber only through the filter separating the main chamber from the plenum chamber.

15. A system comprising:
an enclosure comprising:
  a main chamber;
  a plenum chamber; and
  a filter separating the main chamber from the plenum chamber;
a first pump configured to pump one or more gases into the plenum chamber and then, via the filter, into the main chamber; and
a second pump configured to, while the first pump pumps the one or more gases into the plenum and main chambers:
  maintain negative pressure in the main and plenum chambers by drawing one or more gases from the plenum chamber; and
  cause sterilant vapor within the main chamber to flow from the main chamber into the plenum chamber via the filter and then flow out of the plenum chamber via an outlet of the plenum chamber by drawing one or more gases from the plenum chamber; and
a sterilant vapor generator disposed within the main chamber, the sterilant vapor generator being configured to generate the sterilant vapor and to supply the sterilant vapor to the main chamber, wherein the flow of the one or more gases into the main chamber and the flow of sterilant vapor out of the main chamber pass through the same filter.

16. The system as in claim 15, wherein the filter separating the main chamber from the plenum chamber is an air filter.

17. The system as in claim 15, wherein the filter separating the plenum chamber from the main chamber is a HEPA filter.

18. The system as in claim 15, wherein gas can travel in and out of the main chamber only through the filter separating the main chamber from the plenum chamber.

* * * * *

UNITED STATES PATENT AND TRADEMARK OFFICE
CERTIFICATE OF CORRECTION

PATENT NO.        : 7,674,440 B2
APPLICATION NO.   : 10/583882
DATED             : March 9, 2010
INVENTOR(S)       : Martin It is certified that error appears in the above-identified patent and that said Letters Patent is hereby corrected as shown below:

Column 6
Line 41, change "filter" to --exhaust filter--

Column 7
Line 12, change "fan" to --internal fan--
Line 13, change "fan" to --external fan--
Line 38, delete "as"

Column 8
Line 7, delete "is"
Line 9, change "direction" to --directing--

Signed and Sealed this

Thirty-first Day of August, 2010

David J. Kappos
*Director of the United States Patent and Trademark Office*